(12) United States Patent
Venkataraman et al.

(10) Patent No.: US 10,441,250 B2
(45) Date of Patent: *Oct. 15, 2019

(54) 3D MULTI-PARAMETRIC ULTRASOUND IMAGING

(71) Applicant: ZMK Medical Technologies Inc., Grass Valley, CA (US)

(72) Inventors: Rajesh Venkataraman, Rocklin, CA (US); Saradwata Sarkar, Newcastle, CA (US); Xu Yang, Nevada City, CA (US); Michael Ahmadi, Durham, NC (US)

(73) Assignee: ZMK MEDICAL TECHNOLOGIES INC., Grass Valley, CA (US)

( * ) Notice: Subject to any disclaimer, the term of this patent is extended or adjusted under 35 U.S.C. 154(b) by 136 days.

This patent is subject to a terminal disclaimer.

(21) Appl. No.: 15/289,425

(22) Filed: Oct. 10, 2016

(65) Prior Publication Data

US 2017/0231602 A1  Aug. 17, 2017

Related U.S. Application Data

(60) Provisional application No. 62/238,836, filed on Oct. 8, 2015.

(51) Int. Cl.
*A61B 8/08* (2006.01)
*A61B 8/12* (2006.01)
(Continued)

(52) U.S. Cl.
CPC ............ *A61B 8/5246* (2013.01); *A61B 8/085* (2013.01); *A61B 8/12* (2013.01); *A61B 8/4218* (2013.01); *A61B 8/466* (2013.01); *A61B 8/481* (2013.01); *A61B 8/483* (2013.01); *A61B 8/485* (2013.01); *A61B 8/488* (2013.01); *A61B 8/5207* (2013.01); *G01S 7/52042* (2013.01); (Continued)

(58) Field of Classification Search
CPC .... A61B 8/08; A61B 8/00; A61B 8/12; A61B 8/085; A61B 8/5246; A61B 8/4218; A61B 8/483; A61B 8/481; A61B 8/485; A61B 8/488; A61B 8/5207; A61B 8/466; A61B 5/0095; A61B 5/4381; A61B 8/06; G06T 7/00; G06T 7/0012; G06T 7/337; G06T 7/11; G06T 2207/20081; G06T 2207/30081; G06T 2007/30104; G06T 2207/10136; G06T 2207/30024; G01S 7/52042; G01S 7/52071; G01S 15/894; G01S 15/899; G01S 15/8993; G01S 7/52039
USPC ........................................................ 600/426
See application file for complete search history.

(56) References Cited

U.S. PATENT DOCUMENTS

2014/0276018 A1*  9/2014  Mukdadi ............. A61B 5/4381
                                                          600/426
2018/0008236 A1*  1/2018  Venkataraman ....... A61B 8/085

* cited by examiner

*Primary Examiner* — Jon Eric C Morales
(74) *Attorney, Agent, or Firm* — Marsh Fischmann & Breyfogle LLP; Russell T. Manning (57) ABSTRACT

Systems and methods are disclosed that facilitate obtaining two dimensional (2D) ultrasound images, using two or more ultrasound imaging modes or modalities, to generate 2D multi-parametric ultrasound (mpUS) images and/or to generate a three-dimensional (3D) mpUS image. The different ultrasound imaging modes acquire images in a common frame of reference during a single procedure to facilitate their registration. The mpUS images (i.e., 2D or 3D) may be used for enhanced detection of suspicious regions.

13 Claims, 7 Drawing Sheets

(51) Int. Cl.
*A61B 8/00* (2006.01)
*G06T 7/00* (2017.01)
*G01S 7/52* (2006.01)
*A61B 5/00* (2006.01)
*G01S 15/89* (2006.01)

(52) U.S. Cl.
CPC .......... *G06T 7/0012* (2013.01); *A61B 5/0035* (2013.01); *A61B 5/0095* (2013.01); *A61B 5/4381* (2013.01); *G01S 7/52039* (2013.01); *G01S 15/899* (2013.01); *G01S 15/8993* (2013.01); *G06T 2207/10136* (2013.01); *G06T 2207/20081* (2013.01); *G06T 2207/30081* (2013.01)

Fig. 1

2D Image Storage

FIG. 2A

3D Volume Image

3D MULTI-PARAMETRIC ULTRASOUND IMAGING

CROSS REFERENCE

The present application claims the benefit of the filing date of U.S. Provisional Application No. 62/238,836 having a filing date of Oct. 8, 2016, the entire contents of which is incorporated herein by reference.

FIELD

The present disclosure pertains to the field of medical imaging, and more particularly to the registration of multiple modalities of ultrasound images to generate enhanced contrast between tissue structures for diagnosis and therapy. In one application, multiple modalities of ultrasound images are coregistered into a multimodal ultrasound image to aid urologists in finding target sites for biopsy and/or therapy of a prostate.

BACKGROUND

Medical imaging, including X-ray, magnetic resonance (MR), computed tomography (CT), ultrasound, and various combinations of these techniques are utilized to provide images of internal patient structure for diagnostic purposes as well as for interventional procedures. One application of medical imaging (e.g., 3-D imaging) is in the detection and/or treatment of prostate cancer. According to the National Cancer Institute (NCI), a man's chance of developing prostate cancer increases drastically from 1 in 10,000 before age 39 to 1 in 45 between 40 to 59 and 1 in 7 after age 60. The overall probability of developing prostate cancer from birth to death is close to 1 in 6.

Traditionally either elevated Prostate Specific Antigen (PSA) level or Digital Rectal Examination (DRE) has been widely used as the standard for prostate cancer detection. For a physician to diagnose prostate cancer, a biopsy of the prostate must be performed. This is done on patients that have either high PSA levels or an irregular digital rectal exam (DRE), or on patients that have had previous negative biopsies but continue to have elevated PSA. Biopsy of the prostate requires that a number of tissue samples (i.e., cores) be obtained from various regions of the prostate. For instance, the prostate may be divided into six regions (i.e., sextant biopsy), apex, mid and base bilaterally, and one representative sample is randomly obtained from each sextant. Such random sampling continues to be the most commonly practiced method although it has received criticism in recent years on its inability to sample regions where there may be significant volumes of malignant tissues resulting in high false negative detection rates. Further using such random sampling it is estimated that the false negative rate is about 30% on the first biopsy. 3-D Transrectal Ultrasound (TRUS) guided prostate biopsy is a commonly used method to guide biopsy when testing for prostate cancer, mainly due to its ease of use and low cost.

Recently, it has been suggested that TRUS guidance may also be applicable for targeted focal therapy (TFT). In this regard, adoption of TFT for treatment of prostate cancer has been compared with the evolution of breast cancer treatment in women. Rather than perform a radical mastectomy, lumpectomy has become the treatment of choice for the majority of early-stage breast cancer cases. Likewise, some commentators believe that accurate targeting and ablation of cancerous prostate tissue (i.e., TFT) may eventually replace prostatectomy and/or whole gland treatment as the first choice for prostate treatment. Such targeted treatment has the potential to alleviate side effects of current treatment including, incontinence and/or impotence. Such commentators typically agree that the ability to visualize malignant or cancerous tissue during treatment will be of importance to achieve the accuracy of targeting necessary to achieve satisfactory results.

While TRUS provides a convenient platform for real-time guidance for either biopsy or therapy, it is believed that some malignant tissues can be isoechoic in TRUS. That is, differences between malignant cells and surrounding healthy tissue may not be discernable in a standard ultrasound image. Accordingly, using a standard TRUS image a sole means of guidance has not allowed for visually identifying potentially malignant tissue. Further, speckle and shadows make ultrasound images difficult to interpret, and many cancers are often undetected even after saturation biopsies that obtain several (>20) needle samples. To improve the identification of potentially cancerous regions for biopsy or therapy procedures, it has been proposed to combine different pre-acquired imaging modalities (e.g., MRI, CT etc.), which may provide improved tissue contrast, with a live TRUS image during biopsy or therapy.

Imaging modalities like computed tomography (CT) and magnetic resonance imaging (MRI) can provide information that previously could not be derived from standard TRUS imaging alone. While CT lacks good soft tissue contrast to help detect abnormalities within the prostate, it can be helpful in finding extra-capsular extensions when soft tissue extends to the periprostatic fat and adjacent structures, and seminal vesicle invasions. MRI is generally considered to offer the best soft tissue contrast of all imaging modalities. Both anatomical (e.g., $T_1$, $T_2$) and functional MRI, e.g. dynamic contrast-enhanced (DCE), magnetic resonance spectroscopic imaging (MRSI) and diffusion-weighted imaging (DWI) can help visualize and quantify regions of the prostate based on specific attributes. Stated otherwise, such different imaging modalities may allow for locating suspect regions or lesions within the prostate even when such regions/lesions are isoechoic.

Unfortunately, use of pre-acquired images, from different imaging modalities, with a live TRUS image provides a number of logistic problems. Specifically, use of other different imaging modalities such as MRI has required a patient to attend a separate procedure during which images of the other imaging modality are acquired. Once such images are acquired, (e.g., an MRI or CT image) such images must be registered with a live TRUS image acquired during a biopsy or therapy procedure. Registration of images obtained from different modalities creates a number of complications. This is especially true in soft tissue applications where the shape of an object in two images may change between acquisitions of each image. Further, in the case of prostate imaging the frame of reference (FOR) of the acquired images is typically different. That is, multiple MM volumes are obtained in high resolution transverse, coronal or sagittal planes respectively. These planes are usually in rough alignment with the patient's head-toe, anterior-posterior or left-right orientations. In contrast, TRUS images are often acquired while a patient lies on his side in a fetal position by reconstructing multiple rotated samples 2D frames to a 3D volume. The 2D image frames are obtained at various instances of rotation of the TRUS probe after insertion in to the rectal canal. The probe is inserted at an angle (approximately 30-45 degrees) to the patient's head-toe orientation. As a result the gland in MM and TRUS will need to be rigidly aligned because their relative orientations are unknown at scan time. Also the two glands would have to be compensated for the different gland shapes (non-rigid alignment) due to various factors like bladder filling, pressure of the ultrasound probe on the prostate, etc. It is against this background that the present invention has been developed.

SUMMARY

Aspects of the presented inventions are based on the recognition that, while desirable for diagnosis and treatment, use of different pre-acquired images from different imaging techniques (e.g., MRI) has a number of drawbacks as previously noted. Accordingly, the present inventor has recognized that it would be desirable to provide a multi-parameter image from an ultrasound device during a single imaging and biopsy/treatment session to reduce or eliminate multiple visits and/or registration errors arising from use of differing imaging techniques. More specifically, provided herein is a multi-parametric ultrasound (mpUS) system that operates similar to multi-parameter MRI in that it looks to extract contrast between tissue structures by imaging the different physiological behavior of the gland. Along these lines, the multi-parametric ultrasound system may incorporate standard B-mode ultrasound images, ultrasound elastography images, Doppler ultrasound imaging, photo—acoustic tomography (PAT) imaging, and/or perfusion imaging using micro bubbles to name a few. Each of the contrast mechanisms is available on various high-end ultrasound machines, but like an MRI machine there has not been a way to standardize the protocols between different users, centers and ultrasound machines. Each parametric image/map in ultrasound has its difficulties arising from the fact that the most common ultrasound transducers provide only 2D images and that they are done by hand which reduces the reliability of the results.

The presented system and method (i.e., utility) is unique in that it can combine multiple 2D images (i.e., from a single ultrasound mode or multiple ultrasound modes) into a single 3D volume. In order to produce such a 3D volume, an ultrasound probe is held on a robotic arm that provides control over where the probe is imaging (e.g., prostate) along with the ability to fuse the multiple parametric maps automatically through mechanical registration, though software registration could be used if necessary.

With the probe in the robotic arm and pointing at the target tissue (e.g., prostate) the utility is operable to:
1. Create a 3D B—mode volume from a set of 2D B—mode images
   a. Acquire a set of 2D B—mode images by rotating the probe and reconstruct them into 3D volume
2. Create a 3D elastography volume from a set of 2D elastography images
   a. Acquire a set of 2D elastography (strain wave, shear wave or ARFI) images at each location of the probe before rotating to the next location.
   b. Reconstruct from the acquired 2D images a 3D elastography volume
3. Create 3D+time volume from a set of 2D B—mode images before, during and after the injection of micro—bubbles as contrast agent.
   a. Acquire a set of 2D B—mode images by continuously rotating the probe over a given time and combine them into a 3D volume for that time point.
   b. A time point is defined as the volume created from 2D B—mode images when the probe is rotated from start position to 180 degrees from start position.
   c. Keep combining the 2D B—mode images to get a set of 3D volumes over time.
   d. Apply the 2 compartments Tofts model (or any pharmacokinetic modeling or phenomenological modeling) to the 3D time series data to extract parametric maps
4. Create a 3D Doppler volume from a set of 2D Doppler images.
   a. Acquire a set of 2D Doppler images by rotating the probe and reconstruct them to 3D volume.
5. Create a 3D PAT volume from a set of 2D PAT image.
   a. Acquire a set of 2D PAT image by rotating the probe and reconstruct them to 3D volume Any or all of the 2D images and/or 3D volumes are acquired during a common procedure (e.g., sequentially) and are mechanically registered since the probe is on a robotic arm with no movement other than rotational movement of the probe. In one arrangement, the probe rotation is about an axis that runs through the probe thereby eliminating the distortion on the gland when rotating the probe. Also the rotation of the probe may be controlled by a motor further reducing registration offsets between the images.

Based on all the mpUS images/maps, a computer aided detection algorithm or classifier is applied to detect suspicious regions. The utility then aligns the probe to the suspicious region to take a biopsy sample and/or apply therapy. That is, the utility generates a multi-parametric ultrasound image, analyzes the image to detect suspicious region(s), and provides real-time images to guide biopsy and/or therapy to the suspicious region(s). In the case of prostate imaging/therapy, the utility does a complete 3D mpUS study of the prostate that will be used for automatic detection of one or more suspicious regions and then guides biopsy or therapy of the suspicious region(s) using the device in the same sitting. One uniqueness lies in the ability to standardize the mpUS settings over different ultrasound machines.

DETAILED DESCRIPTION

Reference will now be made to the accompanying drawings, which assist in illustrating the various pertinent features of the present disclosure. Although the present disclosure is described primarily in conjunction with transrectal ultrasound imaging for prostate imaging and therapy, it should be expressly understood that aspects of the present disclosure may be applicable to other medical imaging applications. In this regard, the following description is presented for purposes of illustration and description.

Systems and methods are disclosed that facilitate obtaining two dimensional (2D) ultrasound images, using two or more ultrasound imaging modes or modalities, to generate 2D multi-parametric ultrasound (mpUS) images and/or to generate a three-dimensional (3D) mpUS image. The different ultrasound imaging modes acquire images in a common frame of reference during a single procedure to facilitate their registration. In any case, the mpUS images (i.e., 2D or 3D) may be used for enhanced and/or automated detection of one or more suspicious regions. After identifying one or more suspicious regions, the mpUS images may be utilized with a real-time image to guide biopsy or therapy the region(s). All these processes may be performed in a single medical procedure.

Figure 1:
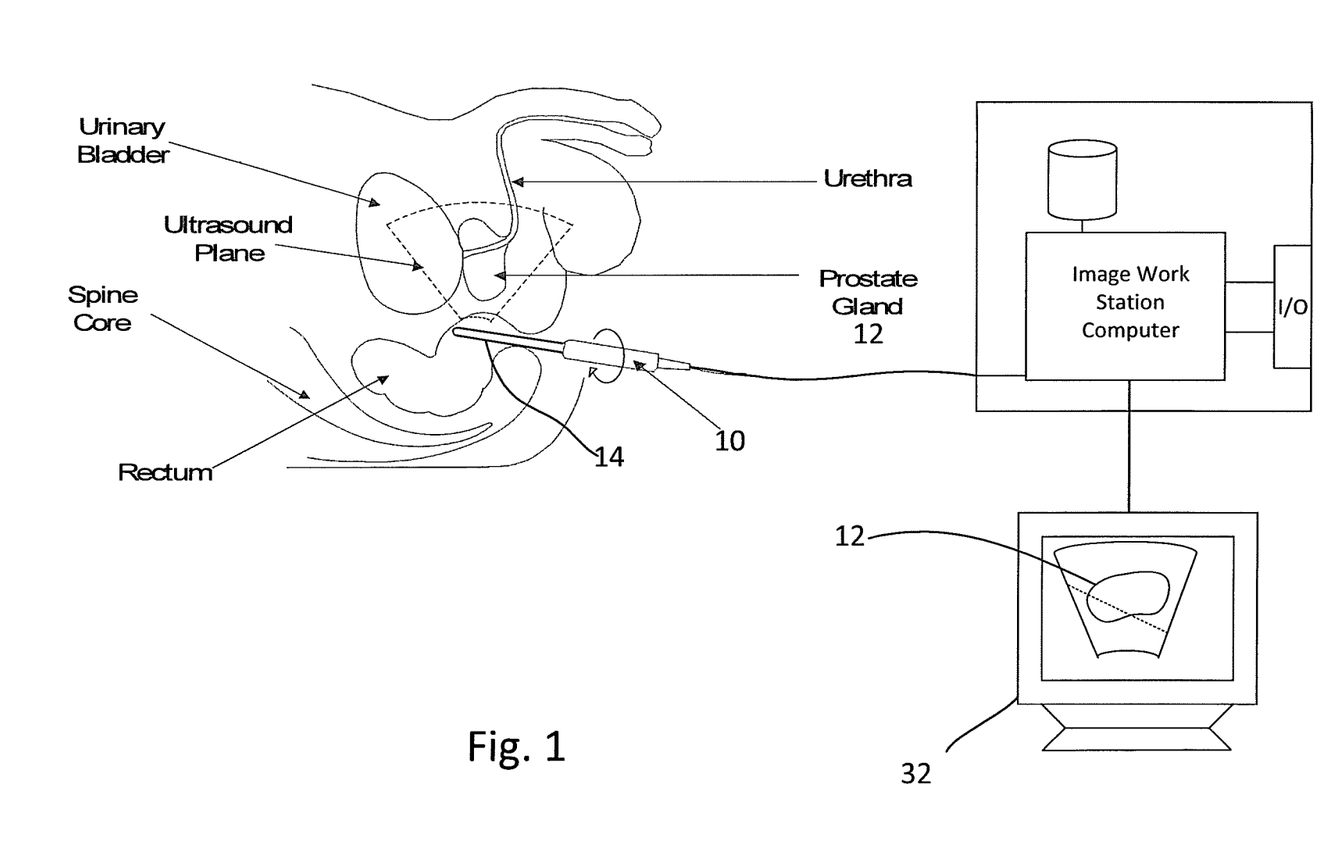
FIG. 1 shows a cross-sectional view of a trans-rectal ultrasound imaging system as applied to perform prostate imaging.
Figure 2A:
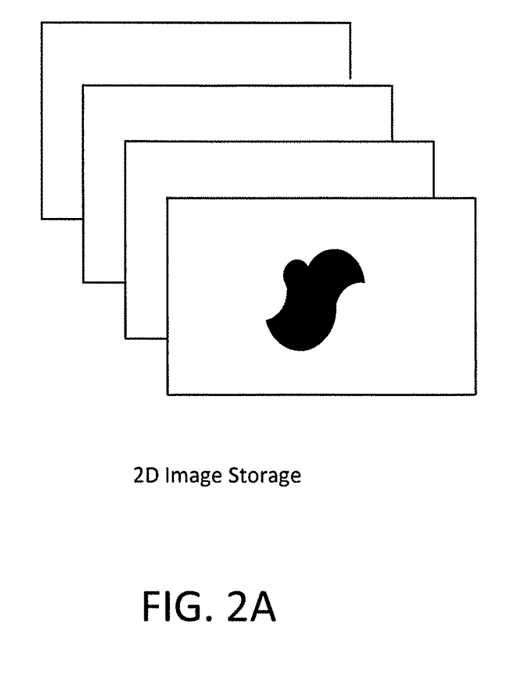
FIG. 2A illustrates two-dimensional images generated by the trans-rectal ultrasound imaging system of FIG. 1.
Figure 2B:
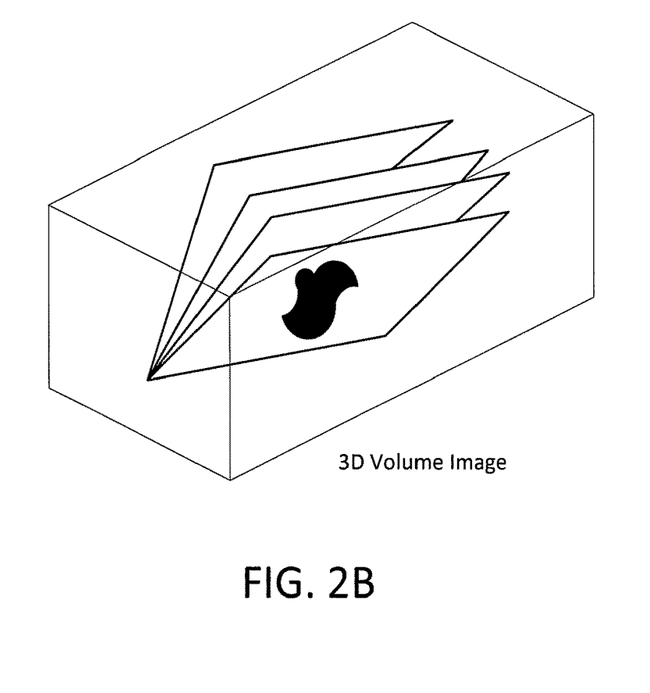
FIG. 2B illustrates a three-dimensional volume image generated from the two dimensional images of FIG. 2A.

FIG. 1 illustrates a transrectal ultrasound probe being utilized to obtain a plurality of 2D ultrasound images of the prostate 12. In such an arrangement, the ultrasound probe may be rotated through an arc (e.g., 180°) to acquire separate images of an area of interest using any one ultrasound imaging mode. The probe may be re-rotated to through the area of interest to acquire additional images using additional modes. The image(s) taken by the probe 10 are provided to an imaging system and may be output to a display 32. In any case, the probe 10 may acquire plurality of individual images while being rotated over the area of interest. See FIGS. 2A-B. Each of these individual images may be represented as a 2D image. See FIG. 2A. Initially, such images may be in a polar or cylindrical coordinate system. In such an instance, it may be beneficial for processing to translate these images into a rectangular coordinate system. In any case, the 2-D images may be combined to generate a 3-D image. See FIG. 2B.

As shown in FIG. 1, the ultrasound probe 10 is a side-fire probe that generates ultrasound waves out of the side surface (e.g., acquisition portion/axis). Other ultrasound probes may be utilized (e.g., end-fire). In any arrangement, it may be desirable to generate an image of the prostate 12 while the probe 10 remains positioned relative to the prostate. If there is little or no movement between acquisitions of the 2D images, these images may be readily registered together. If multiple ultrasound imaging modes are utilized, these images may be registered together to generate a 2D mpUS image and/or to generate a 3D mpUS image. However, manual manipulation of the probe 10 often results in relative and unaccounted movement between the probe and the prostate 12 between subsequent images. Accordingly, it is desirable to minimize relative movement between the probe 10 and the prostrate 12 (i.e., precession, wobble or any other rotational movement of the probe about a fixed axis for image acquisition) for each image of each mode and between different imaging modalities. It is also often desirable for probe 10 to remain fixed relative to the prostrate 12 during biopsy or other treatment procedures such that the desired tissue locations may be targeted accurately. To achieve such fixed positioning of probe 10, it is desirable to interface the probe 10 with a positioning device such as the exemplary positioning device 100 shown in FIG. 3.

Figure 3:
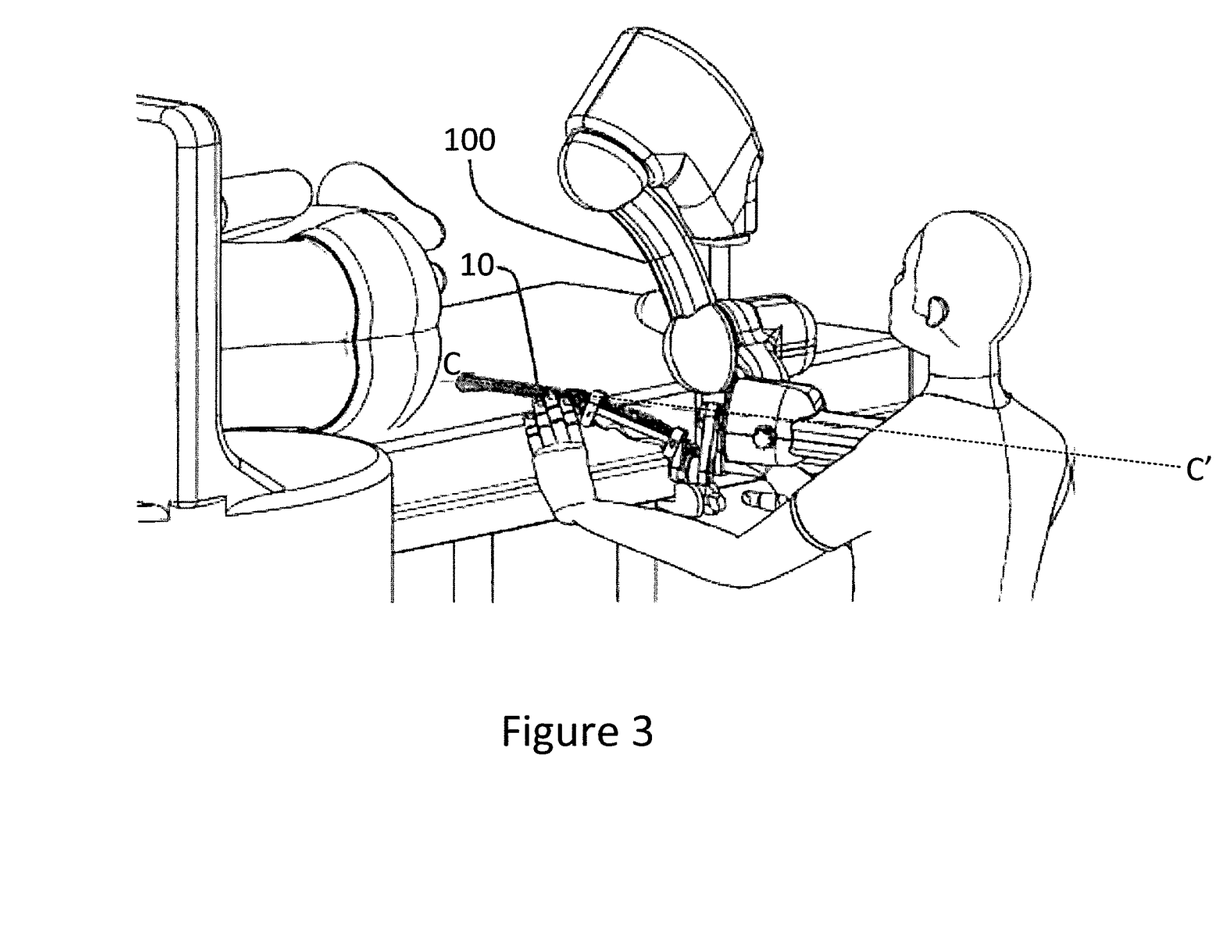
FIG. 3 illustrates use of a positioning device to position an ultrasound imaging device to perform prostate imaging.

The positioning device 100 maintains the acquisition axis of the probe 10 in a known position (e.g., fixed position for a rotational axis) relative to the prostate 12 during image acquisition and provides location information (e.g., frame of reference information) for use with each acquired image. Stated otherwise, in the present embodiment the positioning device 100 maintains an acquisition axis of the probe to a single degree of freedom/movement about a rotational axis C-C' of the positioning device. Thus, all images taken from the probe are in a common frame of reference. In this regard, location outputs from the positioning device 100 may be supplied to a computer and/or imaging device to identify, for example the base location of each image plane and it angular position. Likewise, the output of the probe 10 may be provided to the computer and/or imaging device, and the computer and/or imaging device may utilize this information to more accurately register the images and output (e.g., display) of the imaged object (e.g., prostate). One exemplary positioning device is set forth in International Application Number PCT/CA2007/001076, entitled Apparatus for Guiding a Medical Tool. Another is set forth in U.S. application Ser. No. 11/850,482, entitled Tracker Holder Assembly, the contents of which are fully incorporated herein by reference. Though the positioning devices discussed herein are illustrated as limiting movement about a rotational axis. Limiting movement about a rotational axis is desirable in a number of applications such as internal applications (e.g., transrectal etc.). IN such instances, the acquisition portion of a probe may be shaped to minimize or eliminate tissue displacement during rotation. That is, once the probe is positioned subsequent rotation of the probe does not displace the tissue being imaged. However, it will be appreciated that other positioning devices may be utilized. For instance, for external applications, a positioning device that limits movement to a linear axis may be desirable.

When attached to the positioning device, the probe handle is held by an arm of the device having set of position sensors. These position sensors are connected to the computer of the imaging system via an embedded system interface. Hence, the computer has real-time information of the location and orientation of the probe 10 in reference to a unified rectangular or Cartesian (x, y, z) coordinate system. With the dimensions of the probe 10 taken into the calculations, the 3D orientations of the 2D image planes are known. The ultrasound probe 10 sends signal to the image guidance system 30, which may be connected to the same computer (e.g., via a video image grabber) as the output of the position sensors. In one embodiment, this computer is integrated into the imaging system. The computer therefore has real-time 2D images of the scanning area in memory. The image coordinate system and the arm coordinate system are unified by a transformation. Using the acquired 2D images, a prostate surface (e.g., 3D model of the organ) may be generated and displayed on a display screen in real-time.

The computer system runs application software and computer programs which can be used to control the system components, provide user interface, and provide the features of the imaging system. The software may be originally provided on computer-readable media, such as compact disks (CDs), magnetic tape, or other mass storage medium. Alternatively, the software may be downloaded from electronic links such as a host or vendor website. The software is installed onto the computer system hard drive and/or electronic memory, and is accessed and controlled by the computer's operating system. Software updates are also electronically available on mass storage media or downloadable from the host or vendor website. The software represents a computer program product usable with a programmable computer processor having computer-readable program code embodied therein. The software contains one or more programming modules, subroutines, computer links, and compilations of executable code, which perform the functions of the imaging system. The user interacts with the software via keyboard, mouse, voice recognition, and other user-interface devices (e.g., user I/O devices) connected to the computer system.

While standard B-mode TRUS is a relatively easy and low cost method of generating real-time images and identifying structures of interest, several shortcomings exist. For instance, some malignant cells and/or cancers may be isoechoic to standard B-mode ultrasound. That is, the difference between malignant cells and healthy surrounding tissue may not be apparent or otherwise discernable in a B-mode ultrasound image. Further, speckle and shadows in ultrasound images may make images difficult to interpret. Stated otherwise, standard ultrasound may not, in some instances, provide detailed enough image information to identify tissue or regions of interest.

Other ultrasound imaging modalities may provide significant clinical value, overcoming some of these difficulties. In particular, such modalities may expose tissues or cancers that are isoechoic in standard B-mode TRUS, and therefore indistinguishable from normal tissue in standard ultrasound imaging.

The disclosed system allows for readily registering images acquired from different ultrasound imaging modalities (e.g., multi-parametric ultrasound images/mpUS). If the differing modalities are obtained during a single procedure without intervening patient movement, the different modalities of images may be obtained in a common frame of reference (FOR). That is, images acquired using different ultrasound modes may be acquired for the patient while the patient is in a single position. That is, the probe may be rotated a first time in a first imaging modality, then re-rotated in a different imaging modality one or more additional times. In this regard, one or more ultrasound image modalities, obtained during a common procedure are mechanically registered. However, slight movement between images may be accounted for using additional software registration if necessary.

Differing Ultrasound Imaging Modalities

A number of different ultrasound imaging modalities are available. However, in some instances, additional external hardware is required to generate the differing modality images. In any modality, ultrasound utilizes sound waves with frequencies which are higher than those audible to humans. Ultrasound images are made by sending pulses of ultrasound into tissue using a probe. The sound echoes off the tissue; with different tissues reflecting varying degrees of sound. These echoes are recorded and displayed as an image.

The most well-known ultrasound modality is a B-mode image, which displays the acoustic impedance of a two-dimensional cross-section of tissue. Other types of image can display blood flow, motion of tissue over time, the location of blood, the presence of specific molecules, the stiffness of tissue, or the anatomy of a three-dimensional region.

B-Mode is a two-dimensional ultrasound image display composed of bright dots representing the ultrasound echoes. The brightness of each dot is determined by the amplitude of the returned echo signal. That is, a B-mode image is a 2 dimensional cross sectional view of the underlying structures and is made up of numerous B-mode (brightness mode) scan lines. These images allow for visualization and quantification of anatomical structures, as well as for the visualization of diagnostic and therapeutic procedures. Lesions such as tumors and atherosclerotic plaques can be identified and the extent of disease burden can be quantified. On a grey scale, high reflectivity (bone) is white; low reflectivity (muscle) is grey and no reflection (water) is black. Deeper structures are displayed on the upper part of the screen and superficial structures on the lower part.

Ultrasound elastography (EUS) is a method to assess the mechanical properties of tissue, by applying stress and detecting tissue displacement using ultrasound. EUS is based upon the general principle that stress applied to tissue causes changes within it, which depend on the elastic properties of tissue. There are several EUS techniques depending on the type of stress application and the method used to detect tissue displacement and construct the image. The main techniques used in the clinical practice include strain EUS, shear wave EUS, transient EUS and acoustic radiation force impulse (ARFI) EUS.

The most commonly used method is strain EUS, also described as compression elastography, sonoelastography and real-time elastography. The technique is based on low-frequency compression of the tissue, which is usually applied manually or in some cases using physiological body movement such as respiration or pulsation. The main principle of strain EUS is that a compressive force is applied to tissue causing axial tissue displacement (strain), which is then calculated by comparing the echo sets before and after the compression. Strain EUS is based upon Hooke's law for the calculation of Young's elastic modulus (E), a physical quantity measuring stiffness. By assuming that the applied stress is uniform, the elastic moduli are inversely proportional to the measured strain (E=stress/strain). Strain is the change in size or shape produced by a system of forces, and it is expressed as a ratio (e.g. the change in length per unit length). The force acting on unit area is known as the stress. Strain EUS is actually measuring the relative strain of one area vs another, and displaying it as a map.

This technique allows direct visualization of the strain information as a strain distribution image/map ("the elastogram"), which, for visualization purposes, is greyscale or color coded. The grey or color scale encoding is chosen by the user. Most often red is used for encoding soft tissues, blue for hard tissues and yellow/green for tissue of intermediate stiffness. The elasticity information derived by this method is qualitative or semi-quantitative. The strain of each area is compared with the remaining tissue within the elastogram, so the elastogram is a relative image available for visual comparison only. The semi-quantitative measurement method includes the ratio of the relative strains between the area of interest and a reference area (usually fat). Strain EUS is may be applied in the field of oncology imaging to detect and differentiate malignancy in tissue.

Acoustic radiation force impulse (ARFI) is a type of strain EUS whereby tissue is excited internally by a focused ultrasound pulse, instead of external (manual or physiological) compression. As the ultrasound pulse travels through the tissue, soft tissue experiences larger displacement than hard tissue. After the excitation and displacement by the pulse, the tissue relaxes to its original configuration. The tissue displacement by the original push pulse can be measured using the application of several short-time pulse echoes, which provides data for comparison with the reference image. The technique also results in a qualitative color-coded or greyscale elastogram depicting relative tissue stiffness. This method has the advantage of imaging deeper tissue, not accessible by superficial external compression.

Shear wave EUS is based on a different physical principle. Shear waves are generated within tissue when the conventional ultrasound waves produced by the transducer interact with tissue. Shear waves propagate perpendicular to the axial displacement caused by the ultrasound pulse and attenuate approximately 10 000 times more rapidly than conventional ultrasound. By use of ultrafast algorithms, the velocity of shear waves can be measured and used to evaluate tissue stiffness by calculating the elastic Young's modulus. This technique results in both qualitative color coded elastograms and also quantitative maps either of elasticity or of shear wave velocity.

Transient EUS, also known as vibration-controlled elastography, is a variant of shear wave EUS, whereby the external compression is applied by using a short-tone burst of vibration. The method also relies on the estimation of the velocity of shear waves in tissue, but in order to avoid the bias caused by reflections and interferences occurring between the tissues, vibration is transient, so that forward waves can be separated from the reflected waves.

MicroBubble or contrast-enhanced ultrasound (CEUS) is the application of ultrasound contrast medium to traditional medical ultrasound (e.g., B-mode). Ultrasound contrast agents rely on the different ways in which sound waves are reflected from interfaces between substances. This may be the surface of a small air bubble or a more complex structure. Contrast media are gas-filled microbubbles that are administered intravenously to the systemic circulation. Microbubbles have a high degree of echogenicity (the ability of an object to reflect ultrasound waves). There is a great difference in echogenicity between the gas in the microbubbles and the soft tissue surroundings of the body. Thus, ultrasonic imaging using microbubble contrast agents enhances the ultrasound backscatter, (reflection) of the ultrasound waves, to produce a sonogram with increased contrast due to the high echogenicity difference. Contrast-enhanced ultrasound can be used to image blood perfusion in organs and/or measure blood flow rate in tissue and organs.

There are a variety of microbubbles contrast agents. Microbubbles differ in their shell makeup, gas core makeup, and whether or not they are targeted. Regardless of the shell or gas core composition, microbubble size is fairly uniform. They lie within a range of 1-4 micrometers in diameter. That makes them smaller than red blood cells, which allows them to flow easily through the circulation as well as the microcirculation.

There are two forms of contrast-enhanced ultrasound, untargeted (used in the clinic today) and targeted (under preclinical development). The two methods slightly differ from each other. Untargeted microbubbles are injected intravenously into the systemic circulation in a small bolus. The microbubbles will remain in the systemic circulation for a certain period of time. During that time, ultrasound waves are directed on the area of interest. Targeted contrast-enhanced ultrasound works in a similar fashion, with a few alterations. Microbubbles targeted with ligands that bind certain molecular markers that are expressed by the area of imaging interest are still injected systemically in a small bolus. Microbubbles travel through the circulatory system, eventually finding their respective targets and binding specifically. Ultrasound waves can then be directed on the area of interest. Detection of bound microbubbles may then show that the area of interest is expressing that particular molecular marker, which can be indicative of a certain disease state, or identify particular cells in the area of interest.

Doppler ultrasound uses reflected sound waves to see how blood flows through a blood vessel. It helps users evaluate blood flow through arteries and veins. During Doppler ultrasound, a transducer is passes over the tissue and blood vessels. The transducer sends and receives sound waves that are amplified through a microphone. The sound waves bounce off solid objects, including blood cells. The movement of blood cells causes a change in pitch of the reflected sound waves (called the Doppler Effect). If there is no blood flow, the pitch does not change. Information from the reflected sound waves can be processed by a computer to provide graphs or pictures that represent the flow of blood through the blood vessels. Cancerous tissue typically has differing blood flow characteristics than healthy tissue allowing differentiation of the same. There are several kinds of Doppler ultrasound including color Doppler, pulsed Doppler and power Doppler. Any of these modalities may be utilized.

Photoacoustic tomography (PAT), or Photoacoustic computed tomography (PACT), is an ultrasound analysis technique based on the reconstruction of an internal photoacoustic source distribution from measurements acquired by scanning ultrasound detectors over a surface that encloses the source under study.

The PAT source is produced inside the tissue by the thermal expansion that results from a small temperature rise, which is caused by the absorption of externally applied radiation of pulsed electromagnetic (EM) waves. PAT is also called optoacoustic tomography (OAT) or thermoacoustic tomography (TAT), with the term "thermoacoustic" emphasizing the thermal expansion mechanism in the PA generation. OAT refers particularly to light-induced PAT, while TAT is used to refer to rf-induced PAT.

PAT typically involves optical excitation, ultrasonic detection, and image formation. A short-pulsed laser is usually used to produce ultrasound in biological tissue efficiently. The amplitude of the photoacoustic pressure depends on the optical energy deposition as well as the thermal and mechanical properties of the tissue. Because either unscattered or scattered photons can produce photoacoustic signals, photoacoustic waves can be generated deeply in biological tissue. Because the ultrasonic scattering coefficient in tissue is 2-3 orders of magnitude less than the optical counterpart, high spatial resolution can be achieved by detecting the photoacoustic waves. Consequently, PAT allows for high-resolution optical-contrast imaging.

Generating mpUS Image

Figure 4A:
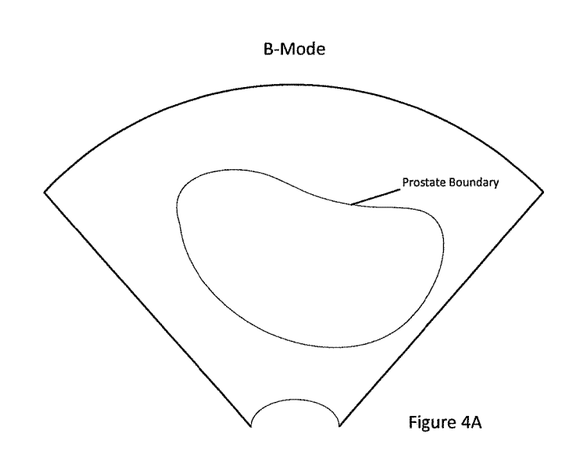
FIGS. 4A-4C illustrate corresponding 2D images acquired using different ultrasound modalities.
Figure 4B:
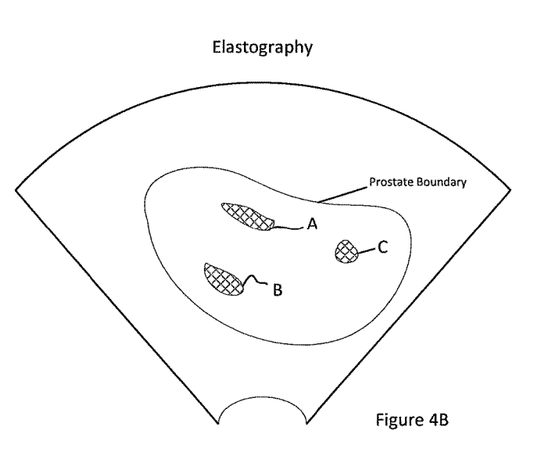
Figure 4C:
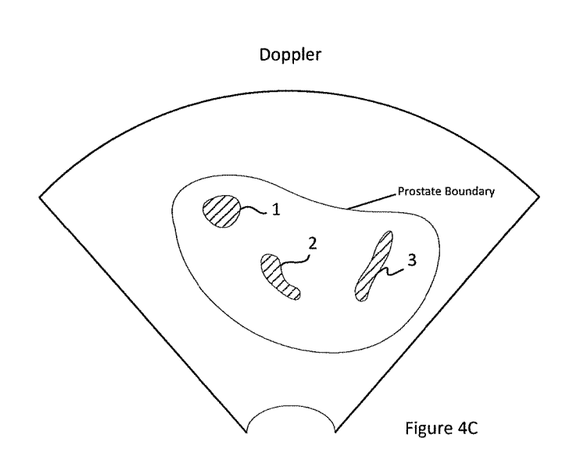
Figure 4D:
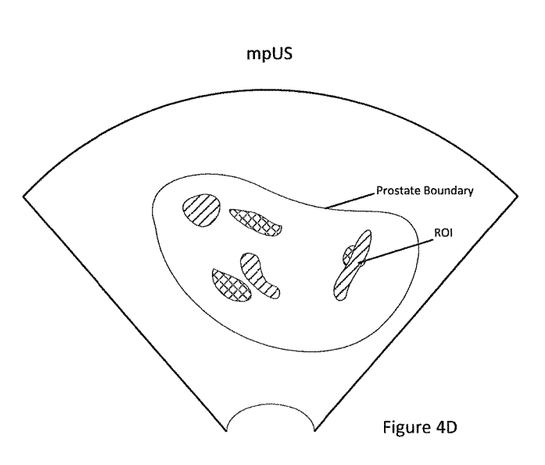
FIG. 4D illustrates an mpUS generated via registration of the images of FIGS. 4A-4C.

When the probe is utilized in conjunction with the positioning device, two or more sets of different ultrasound modalities images may be registered to generate a series of 2D mpUS and/or a 3D mpUS volume. FIGS. 4A-4D illustrate highly simplified ultrasound images for three ultrasound imaging modalities (FIGS. 4A-4C) and a mpUS image (FIG. 4D) generated from the three ultrasound imaging modalities. Each of the illustrated images is a 2D image for purposes of simplification. However, it will be appreciated that 3D images/volumes may be utilized as well. As shown in FIG. 4A, in a first rotational scan a standard B-Mode ultrasound image is acquired. In the present example, the image is of a patient's prostate. After the first image set is acquired, the probe is re-rotated using a second imagining modality. In the present example, an elastography ultrasound is performed during the second scan. See FIG. 4B. As shown in the exemplary scan, a number of areas in the scan (A, B and C) having an elasticity above or below a predetermined threshold are illustrated. After the elastography image is obtained, the probe may again be re-rotated using a third imagining modality. In the present example, a Doppler image is performed during the third scan to identify areas (1, 2 and 3) of blood flow above or below a predetermined threshold. Additional or different scans may be performed. FIG. 4D illustrates the registration of the three images into a mpUS image. This image with multiple modes of information may then be analyzed to identify potential regions of interest.

In one arrangement, user may manually analyze one or more mpUS images to manually identify regions of interest in each mpUS image. In this regard, the use of, for example, a standard b-mode image with a registered elastography image and registered Doppler image may allow the user to better identify tissues regions of interest, for instance, based on the user's experience. Upon identifying such a region(s) (e.g., overlap of elastography area C with Doppler area 3), the identified region(s) may be saved by the system. The system may then be used to align the probe with the region of interest to provide a real-time image including the identified region of interest. Accordingly, such a real-time image may be utilized to guide a needle or other therapy applicator to the point of interest.

In a further arrangement, one or more points of interest or regions of interest (ROI) may be automatically identified using the mpUS image. In this regard, the mpUS images contain a rich set of tissue data that may be algorithmically analyzed. That is, an algorithm or classifier may be utilized to identify regions of interest.

Classifier algorithm information collection initially entails the imaging of tissues having regions known to be cancerous or otherwise of interest (e.g., lesions) using the different imaging modalities for classification. In this regard, images for each modality may be taken of tissues (e.g., prostates) having known cancerous regions/lesions for a large group of patients. The images are collected and used to compile a database of images having known cancerous regions. Once the images are collected for each imaging modality, histological data for the imaged tissue may be acquired. That is, histological slices from the actual imaged tissues (e.g., prostates) corresponding to the 2D and/or 3D images may be obtained. Such histological data may entail a histologist examining and/or testing the histological slices and labeling the slices and corresponding images with pertinent information to generate ground truth images. The ground truth images for each modality are all mapped to a common frame of reference and may each contain markers that identify/label every location of the image (e.g., prostate) as cancerous, non-cancerous or otherwise. Further, the type of cancer may also be labeled.

The database of images whose cancer/lesion characteristics are known is referred to as ground truth images. The ground truth images may be utilized to identify correlations between the image data and the known cancerous tissue and non-cancerous tissue. For instance, image intensity, blood flow, elasticity etc. may be correlated to the existence of cancerous tissue. Such correlations may be identified individually for each imaging modality. Furthermore, correlations between known tissue types and combinations of any two or more of the imaging modalities may be identified. For example, the correlations between tissue types and an mpUS image formed of B-mode images and elastography images may be identified. By way of example only, tissue with intensity above/below a predetermined threshold and with an elasticity above/below a predetermined threshold may indicate potentially cancerous tissue. Accordingly, these correlations may be subsequently utilized during multi-modal imaging to classify tissue in real-time or near real-time images. That is, if areas in the currently imaged tissue have predetermined correlations between imaging modalities, these regions may be identified (e.g., automatically) as cancerous or otherwise of interest. In any case, once training images and histological data is obtained for a set of ground truth images, correlations may be identified for the different modalities or different combinations of the modalities.

The generation of correlations or classifiers is initially performed in an offline model training system (not shown). Inputs to the system include ultrasound images (i.e., for each imaging modality) of tissue and corresponding histological data for the imaged tissue. The histology data and the ultrasound images in the patient database are used to generate ground truth information used to train a classifier or multiple classifiers (e.g., depending on the combination of imaging modalities). Once ground truth tumor information is generated, regions of interest (ROIs) from different classes of the ground truth information may be identified. For instance, a feature extraction process may be performed on each different class to generate extracted feature vectors. That is, cancerous regions and benign regions in the training images are known. The features to describe different ROIs are extracted. The feature sets then represent each image feature. Also, the best feature sets may be selected through a feature selection procedure. Then such feature vectors from each ROI may be used as inputs in a classifier training process to produce trained classifiers that the multi-parameter ultrasound imaging system may utilize to identify suspect regions in a current mpUS image.

One method for generating tumor ground truth information for prostate images can be summarized as follows: initially, in the training dataset, the prostate boundary of the 2D images (or 3D volumes sliced into 2D image slices) is segmented by a semi-automatic or automatic segmentation algorithm. Histology data is also incorporated into the 2D images with cancerous/lesion/tumor regions marked out by a histologist or urologists. After this step, the cancerous regions and benign regions (ROIs) in the training images are known. Then a set of feature vectors to describe different ROIs is extracted by image processing algorithms. The feature vectors may include, without limitation, statistical features, gradient features and Gabor filtering features. The features with the most discriminant power are selected through a feature selection algorithm. As a result, each ROI with known class label is digitized by a feature vector. They are used as training samples to train a classifier. The best parameters associated with a classifier are determined through the training procedure. This is offline model training. For a new patient, the system analyzes an mpUS image and provides initial suggested biopsy or therapy regions (ROIs) in the mpUS image based on the trained classifier. One method of training a classifier is set forth in co-owned U.S. Pat. No. 8,175,350, which is incorporated herein as if set forth in full.

Returning to the example of FIGS. 4A-4D, a trained classifier may be operative to automatically identify an ROI based on an overlap of outlying elastic properties and outlying blood flow properties. Accordingly, such a ROI may be flagged for a user and or saved to the system. In any arrangement, once ROIs are identified, these ROIs may be accessed for biopsy or therapy. Again, such biopsy or therapy may be performed during the same procedure where the images are acquired.

Figure 5:
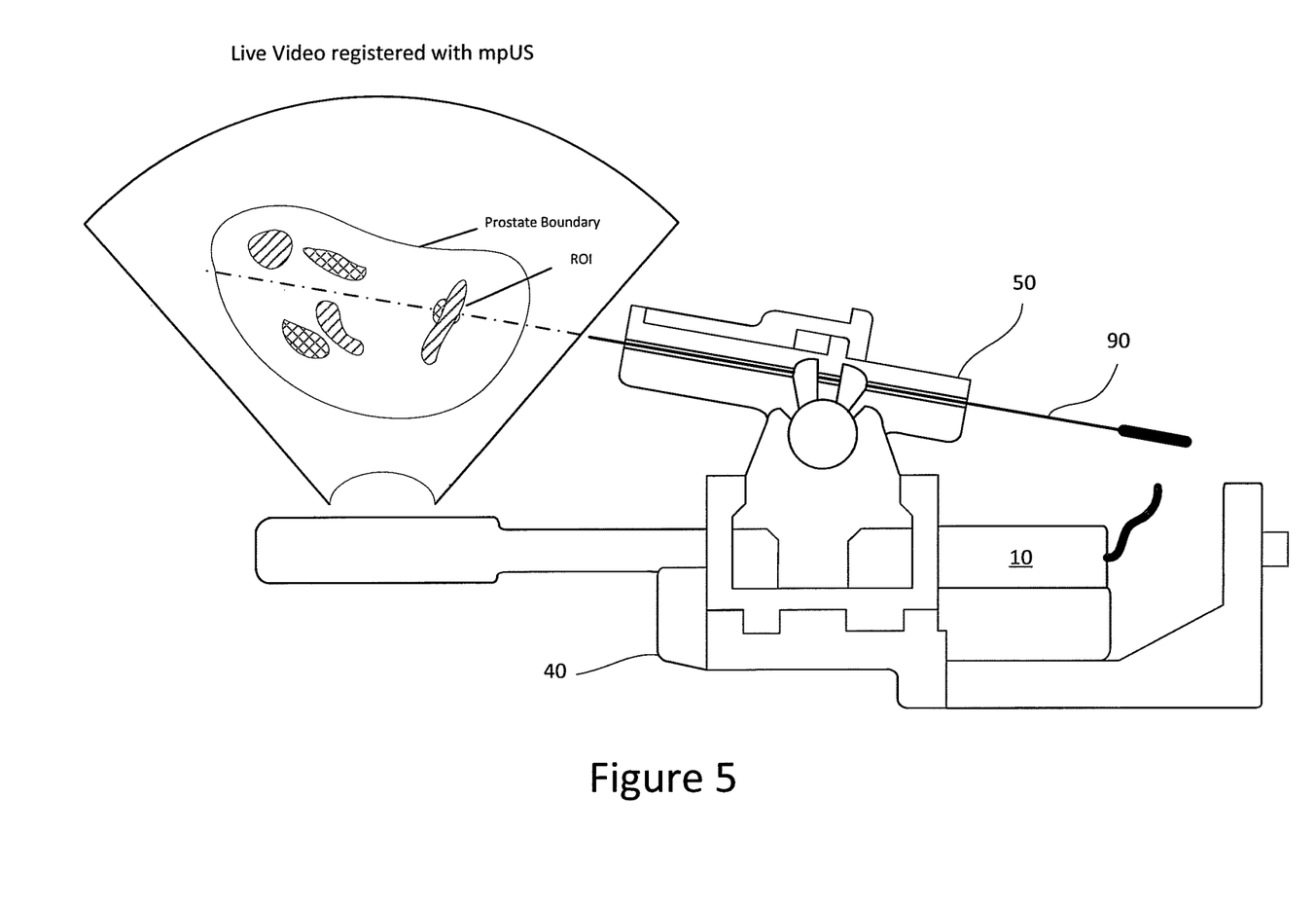
FIG. 5 illustrates targeting a ROI using an mpUS image.
Figure 6:
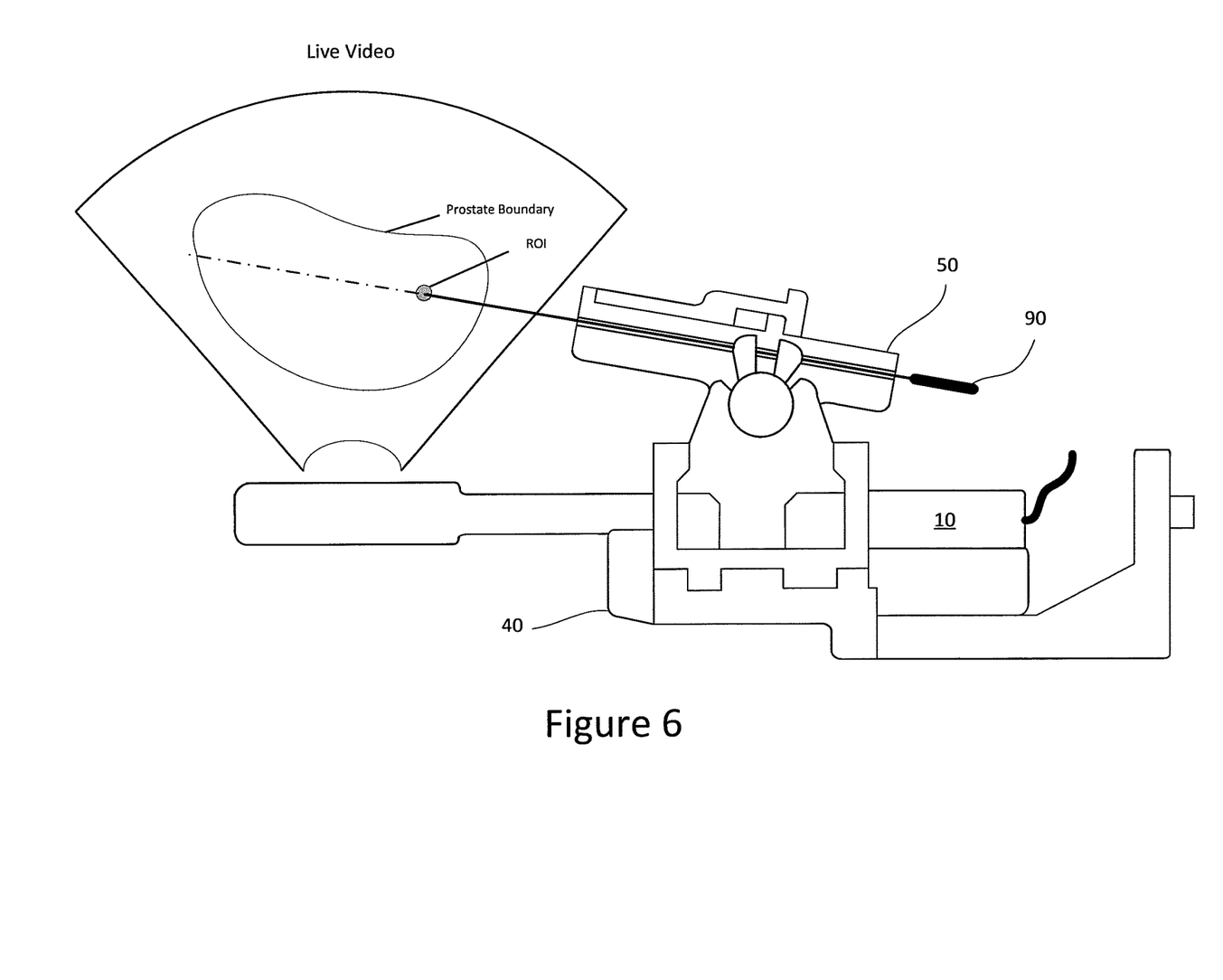
FIG. 6 is a modification of FIG. 5.
Figure 7:
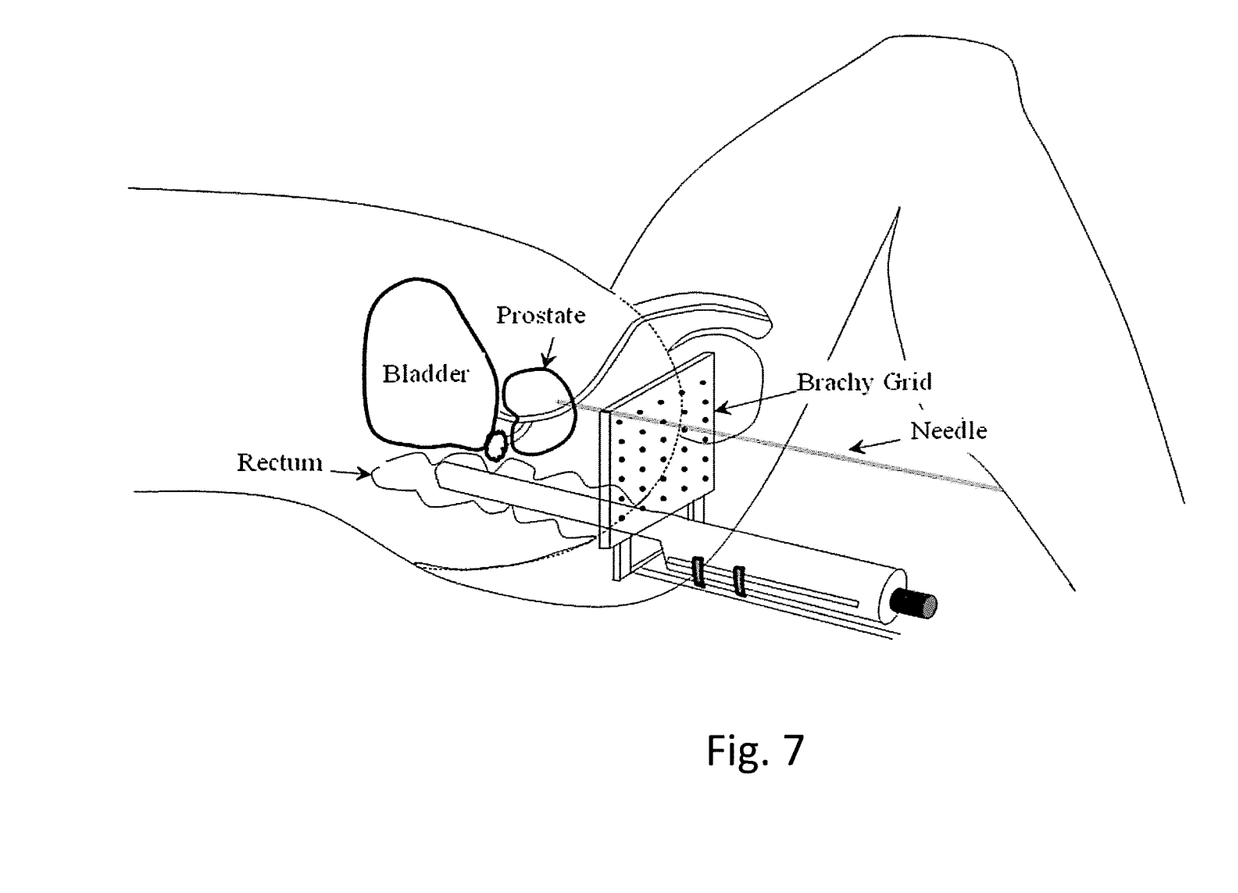
FIG. 7 illustrates using an external grid to target a ROI.

FIG. 5 shows one biopsy therapy device that is incorporated with the probe 10. As shown, a cradle assembly 40, which connects to the positioning system, supports the probe 10 during image acquisition. Such a cradle assembly is set forth in U.S. Provisional Patent Application No. 62/189,352, which is incorporated by reference in its entirety. The cradle assembly 40 includes a guide assembly 50, which supports a biopsy needle or therapy delivery trocar 90 within a plane of the probe. Along these lines, once a region of interest is identified, the probe may be rotated to align with the ROI and the guide assembly rotates to align a trajectory of the needle/trocar 90 with the ROI. The needle/trocar may then be advanced to the ROI under real time guidance. See FIG. 6. Of note in FIG. 6, rather than showing a live ultrasound image (e.g., B-mode) registered with the mpUS image, the real-time image simply includes a target point ROI that was identified from the mpUS image. In this example, the system may use a real time image or volume to provide guidance for an introducer (e.g., needle, trocar etc.) of a targeted focal therapy (TFT) device. Such TFT devices typically ablate cancer foci within the prostate using any one of a number of ablative modalities. These modalities include, without limitation, cryotherapy, brachytherapy, targeted seed implantation, high-intensity focused ultrasound therapy (HIFU) and/or photodynamic therapy (PDT). In another arrangement, the needle trocar may be supported by an external system separate from the probe. See FIG. 7.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such or other embodiments and with various modifications required by the particular application(s) or use(s) of the present invention. It is intended that the appended claims be construed to include alternative embodiments to the extent permitted by the prior art.

The invention claimed is:

1. A method for use with ultrasound imaging, comprising:
    positioning an ultrasound probe in a positioning device proximate to patient tissue, wherein said positioning device limits movement of an acquisition portion of said ultrasound probe to a single axis of movement;
    first acquiring from the ultrasound probe, a first set of images of the patient tissue as the acquisition portion of the ultrasound probe moves over said single axis a first time, wherein said first set of images are acquired using a first ultrasound imaging modality;
    second acquiring, from the ultrasound probe, a second set of images of the patient tissue as the acquisition portion of the ultrasound probe moves over said single axis a second time, wherein said second set of images are acquired using a second ultrasound imaging modality;
    third acquiring, from the ultrasound probe, a third set of images of the patient tissue as the acquisition portion of the ultrasound probe moves over said single axis a third time, wherein said third set of images are acquired using a third ultrasound imaging modality;
    registering said first, second and third sets of ultrasound images acquired using said first second and third ultrasound imaging modalities into a common frame of reference to generate a multi-parametric ultrasound (mpUS) image of the patient tissue;
    applying at least a first classifier to at least a portion of said mpUS image; and
    identify one or more regions of interest by identifying one or more first areas, one or more second areas and one or more third areas of said mpUS image above or below a predetermined first modality threshold, above or below a predetermined second modality threshold, and above or below a predetermined third modality threshold, respectively.

2. The method of claim 1, wherein identifying one or more regions of interest comprises:
    identifying one or more regions covered by at least two of said first, second and third areas that are above or below said first, second and third modality thresholds, respectively.

3. The method of claim 2, wherein identifying one or more regions of interest comprises:
    identifying one or more regions at least partially covered by each of said first, second and third areas that are above or below said first, second and third modality thresholds, respectively.

4. The method of claim 1, further comprising:
    first obtaining, from the positioning device, first position information for each of said first set of images as the acquisition portion of the ultrasound probe moves over said single axis the first time;
    second obtaining, from the positioning device, second position information for each of said second set of images as the acquisition portion of the ultrasound probe moves over said single axis the second time; and
    third obtaining, from the positioning device, third position information for each of said third set of images as the acquisition portion of the ultrasound probe moves over said single axis the third time.

5. The method of claim 4, wherein said first, second and third position information is utilized to register said first, second and third sets of ultrasound images into the common frame of reference.

6. The method of claim 1, wherein said first second and third acquiring steps and said registering steps are performed during a single procedure while a patient remains in a substantially common position.

7. The method of claim 6, further comprising:
    displaying the mpUS image and one or more regions of interest within the mpUS image to a display screen.

8. The method of claim 7, further comprising:
    aligning the acquisition portion of the ultrasound probe to image one of the regions of interest to provide a live image of the region of interest and aligning a needle guide assembly with the region of interest.

9. The method of claim 8, further comprising:
    guiding a needle or trocar through the aligned needle guide assembly to direct a needle to the region of interest in the patient tissue.

10. The method of claim 1, wherein said first second and third ultrasound imaging modalities are selected from a group of imaging modalities including:
    B-mode;
    elastography mode;
    b-mode with injection of contrast agent;
    Doppler mode; and
    PAT mode.

11. The method of claim 1, wherein said first, second and third acquiring step further comprises;
    first acquiring a first set of 2D images and generating a first 3D volume from said first set of 2D images;
    second acquiring a second set of 2D images and generating a second 3D volume from said second set of 2D images;
    third acquiring a third set of 2D images and generating a third 3D volume from said third set of 2D images.

12. The method of claim 11, wherein registering comprises registering said first, second and third 3D volumes.

13. The method of claim 12 further comprising:
    performing a non-rigid registration between any two of said 3D volumes.

* * * * *